United States Patent [19]
Herrin et al.

[11] Patent Number: 6,077,379
[45] Date of Patent: *Jun. 20, 2000

[54] METHOD OF FORMING DISPOSABLE UNDERGARMENT

[76] Inventors: Robert M. Herrin, 5935 Groveline Dr., Orlando, Fla. 32810; John M. Tharpe, 2606 Northgate, Albany, Ga. 31707

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/959,146

[22] Filed: Oct. 28, 1997

Related U.S. Application Data

[62] Division of application No. 08/667,518, Jun. 21, 1996, Pat. No. 5,879,500.

[51] Int. Cl.[7] ........................................... A61F 13/15
[52] U.S. Cl. ................... 156/269; 156/73.1; 156/163; 156/164; 156/229; 156/308.4
[58] Field of Search ........................ 156/229, 164, 156/163, 161, 73.1, 250, 308.2, 309.6, 308.4, 269, 267; 604/396, 392, 385.2; 19/148

[56] References Cited

U.S. PATENT DOCUMENTS

| | | |
|---|---|---|
| 2,034,716 | 3/1936 | Dreyfus . |
| 2,283,137 | 5/1942 | Fine . |
| 2,682,294 | 6/1954 | Langer . |
| 2,702,406 | 2/1955 | Reed . |
| 3,081,772 | 3/1963 | Brooks et al. . |
| 3,161,563 | 12/1964 | Walker et al. . |
| 3,417,751 | 12/1968 | Murdoch . |
| 3,461,872 | 8/1969 | McConnell et al. . |
| 3,661,680 | 5/1972 | Gore ..................................... 156/552 X |
| 3,765,973 | 10/1973 | Kramer . |
| 3,828,367 | 8/1974 | Bourgeois ........................... 156/164 X |
| 3,828,784 | 8/1974 | Zoephel . |
| 4,151,031 | 4/1979 | Goad et al. . |

(List continued on next page.)

FOREIGN PATENT DOCUMENTS

| | | |
|---|---|---|
| 0 234 658 | 2/1987 | European Pat. Off. . |
| 0 405 575 A1 | 1/1991 | European Pat. Off. . |
| 0 510 715 A1 | 10/1992 | European Pat. Off. . |
| 0 631 766 A1 | 1/1995 | European Pat. Off. . |
| 2219636 | 9/1974 | France . |
| 1-298203 | 12/1989 | Japan . |
| 3-205053 | 9/1991 | Japan ..................................... 604/396 |
| 3-231660 | 10/1991 | Japan . |
| 4-028363 | 1/1992 | Japan . |
| 4-161152 | 6/1992 | Japan ................................. 604/385.2 |
| 2 235 125 | 2/1991 | United Kingdom . |
| 2 257 652 | 1/1993 | United Kingdom . |
| WO 95/27461 | 10/1995 | WIPO ..................................... 156/164 |

*Primary Examiner*—Jeff H. Aftergut
*Attorney, Agent, or Firm*—Allen, Dyer, Doppelt, Milbrath & Gilchrist, P.A.

[57] ABSTRACT

A disposable undergarment forming apparatus and methods are provided for forming disposable undergarments. The apparatus preferably includes a core former positioned to form a stream of undergarment cores. The core former includes a mat securer positioned to secure each of a plurality of undergarment mats to a sheet of a polymeric material and a first separator positioned downstream from the mat securer for separating the stream of undergarment cores into a plurality of individual cores. An elastic waistband former preferably is positioned adjacent the core former for forming elastic waistbands. A waistband securer is positioned downstream from the core former and positioned to receive the elastic waistbands from the elastic waistband former for securing the waistbands to the plurality of individual undergarment cores to thereby form a chain of a plurality of undergarments. A folder is positioned downstream from the waistband securer for folding each of the plurality of undergarments of the chain. A side connector is positioned downstream from the folder for connecting at least the side peripheries of the waistbands of the plurality of undergarments of the chain. The apparatus also preferably includes a second separator positioned downstream from the side connector for separating the plurality of undergarments of the chain into individual disposable undergarments.

6 Claims, 12 Drawing Sheets

U.S. PATENT DOCUMENTS

| | | |
|---|---|---|
| 4,205,679 | 6/1980 | Repke et al. . |
| 4,488,927 | 12/1984 | Hooper . |
| 4,610,681 | 9/1986 | Strohbeen et al. . |
| 4,650,530 | 3/1987 | Mahoney et al. ................... 156/73.1 |
| 4,677,695 | 7/1987 | Van Gompel et al. . |
| 4,743,241 | 5/1988 | Igaue et al. . |
| 4,747,846 | 5/1988 | Boland et al. . |
| 4,771,483 | 9/1988 | Hooreman et al. ........................ 2/402 |
| 4,801,345 | 1/1989 | Dussaud et al. . |
| 4,822,435 | 4/1989 | Igaue et al. . |
| 4,834,740 | 5/1989 | Suzuki et al. . |
| 4,854,985 | 8/1989 | Soderlund et al. . |
| 4,862,673 | 9/1989 | Francioni . |
| 4,863,542 | 9/1989 | Oshefsky . |
| 4,892,528 | 1/1990 | Suzuka et al. . |
| 4,904,251 | 2/1990 | Igaue et al. . |
| 4,909,804 | 3/1990 | Douglas . |
| 4,925,520 | 5/1990 | Beaudoin et al. . |
| 4,943,340 | 7/1990 | Ujimoto et al. . |
| 5,043,036 | 8/1991 | Swenson . |
| 5,055,103 | 10/1991 | Nomura et al. . |
| 5,064,489 | 11/1991 | Ujimoto et al. . |
| 5,080,741 | 1/1992 | Nomura et al. . |
| 5,147,487 | 9/1992 | Nomura et al. . |
| 5,163,932 | 11/1992 | Nomura et al. . |
| 5,196,000 | 3/1993 | Clear et al. . |
| 5,308,345 | 5/1994 | Herrin . |
| 5,330,598 | 7/1994 | Erdman et al. ........................ 156/164 |
| 5,421,924 | 6/1995 | Ziegelhoffer et al. ................. 156/73.1 |
| 5,439,459 | 8/1995 | Tanji et al. ........................ 156/164 X |

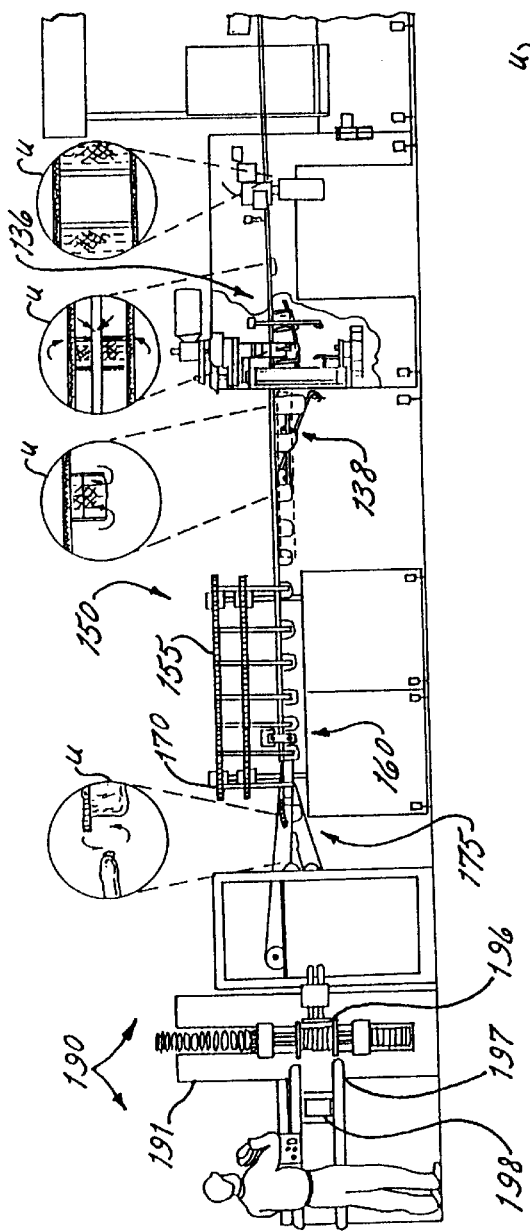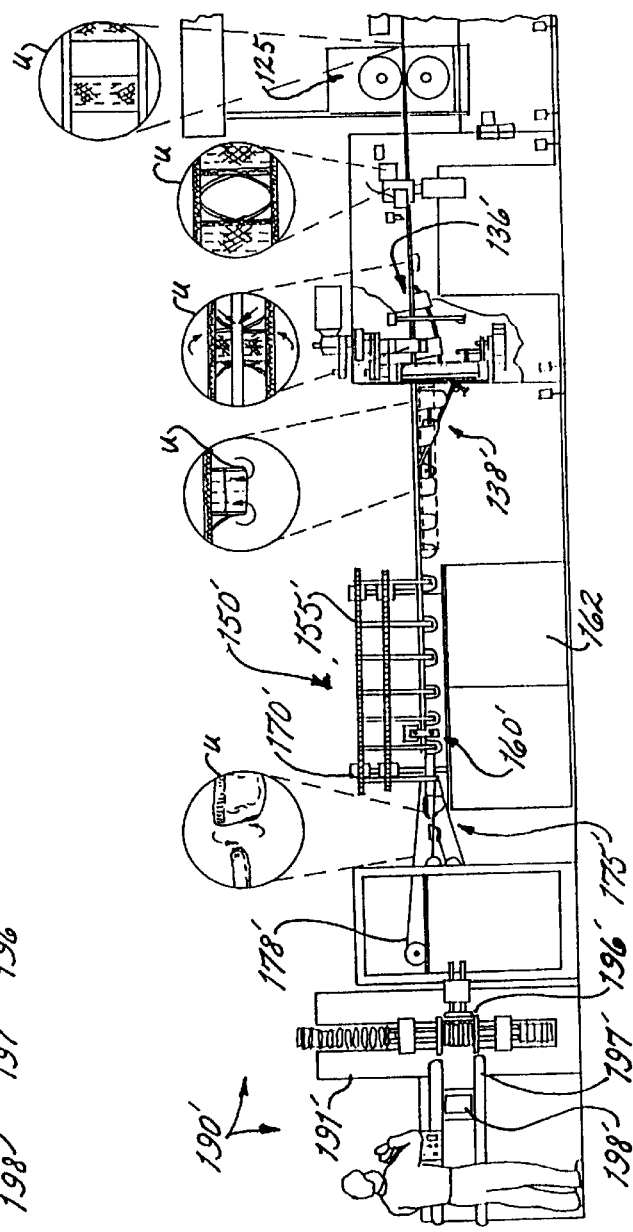

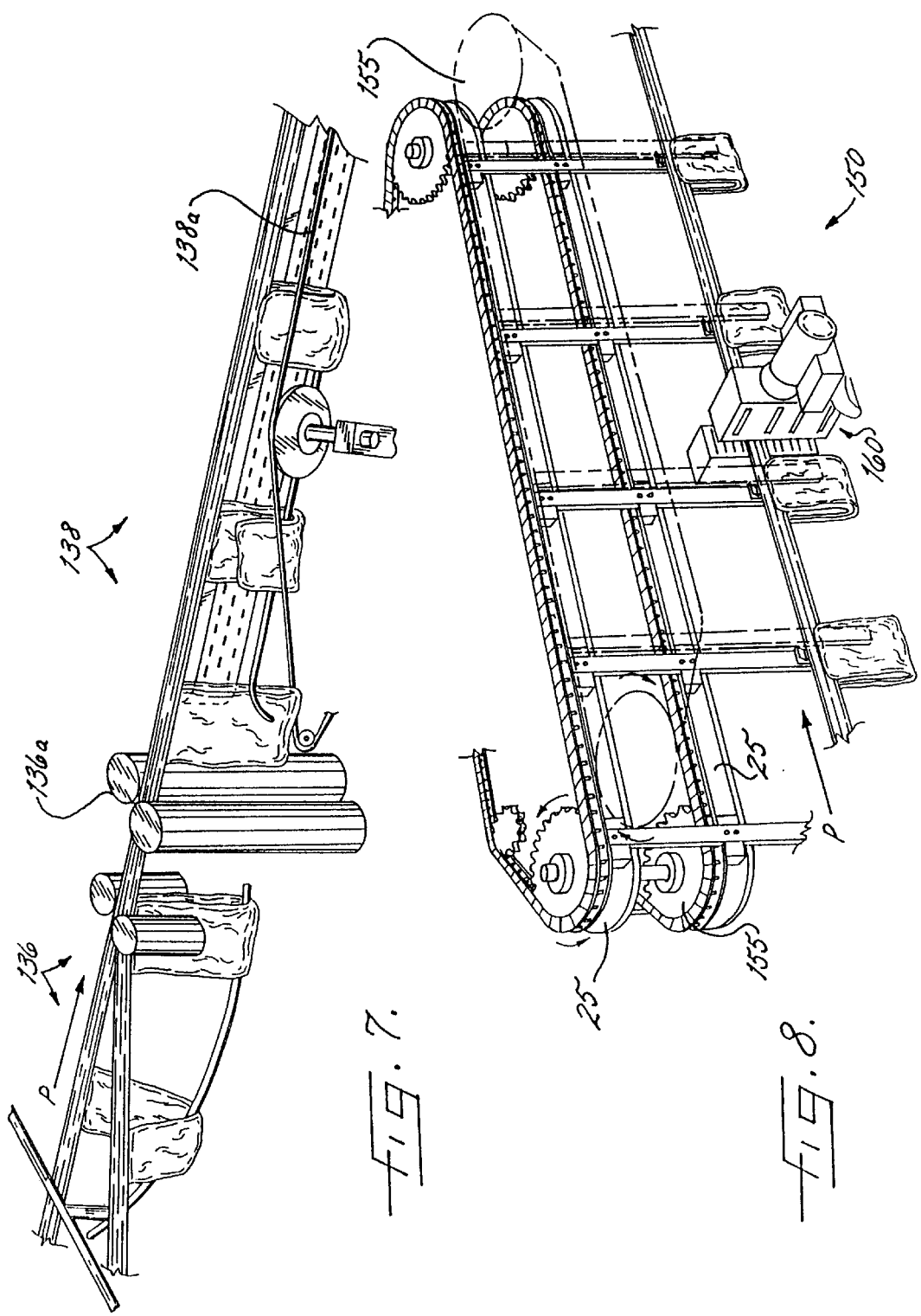

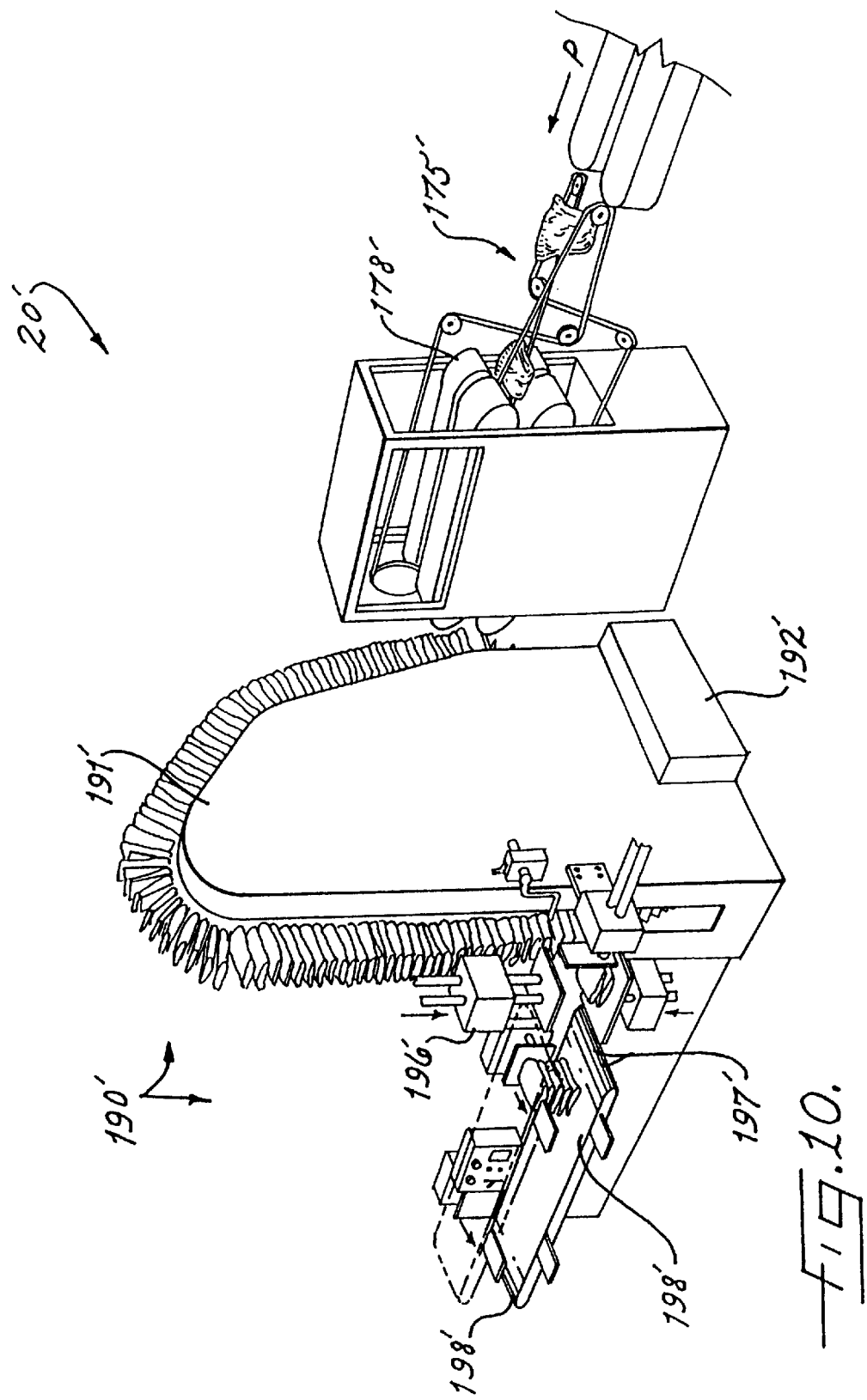

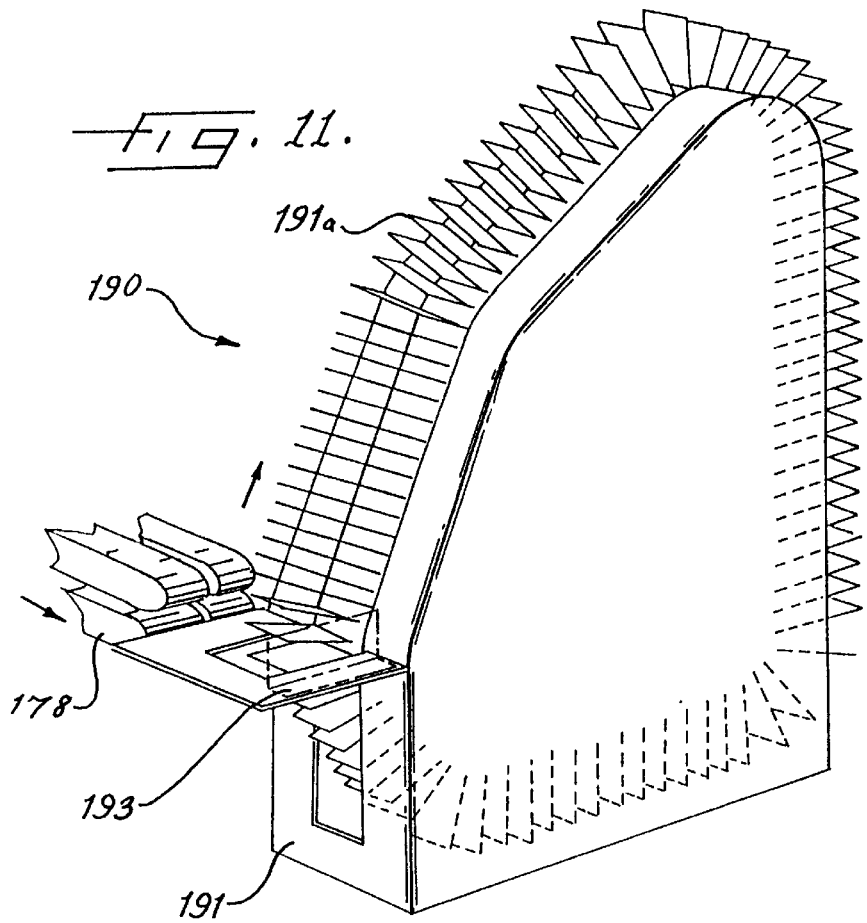
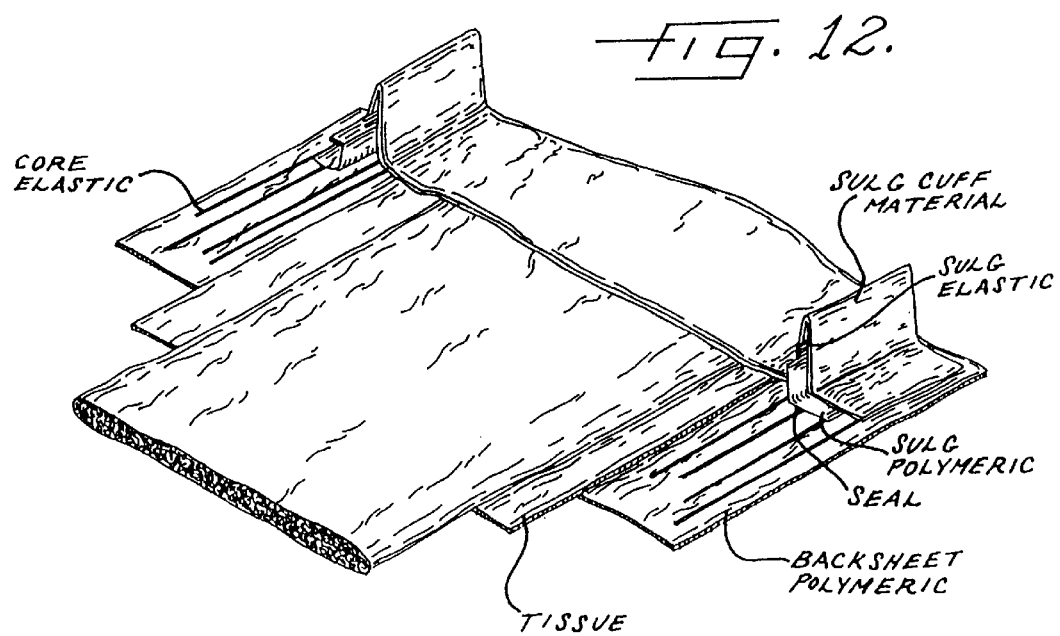

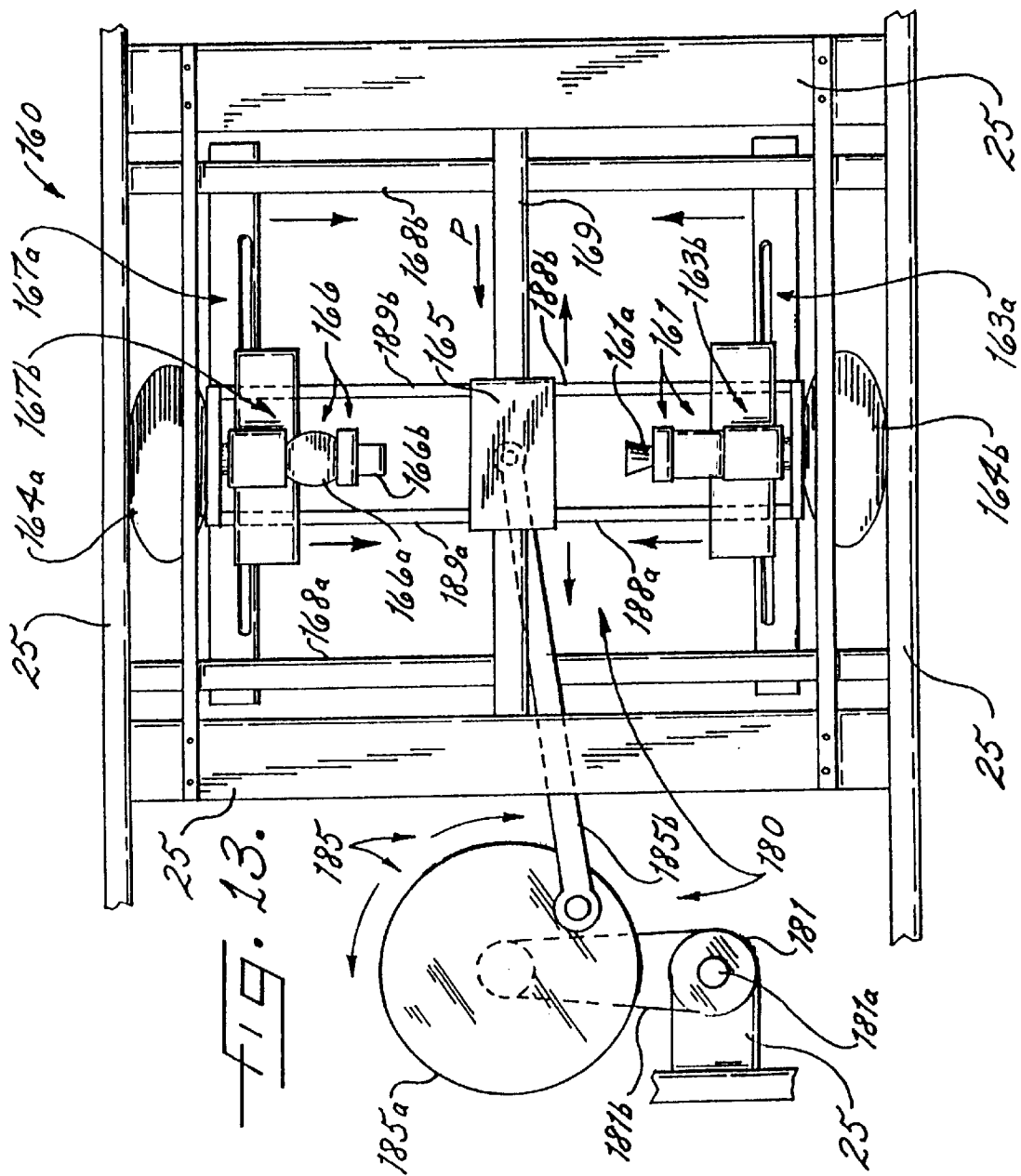

METHOD OF FORMING DISPOSABLE UNDERGARMENT

This application is a divisional of U.S. Ser. No. 08/667,518 filed on Jun. 21, 1996 now U.S. Pat. No. 5,879,500.

FIELD OF THE INVENTION

This application is related to the manufacture of disposable products and, more particular, to a disposable undergarment apparatus and method of forming undergarments.

BACKGROUND OF THE INVENTION

Over the years, consumers have shifted demand from cloth diapers to disposable diapers for infants and toddlers. This demand has increased and developed the disposable diaper industry into a major industry. As this industry developed, consumers preferred and often demanded improvements in disposable products which included better core absorbency, products which are easier to fasten, detach, and reattach side peripheries of the waistbands, various sizes of products for various weights and sizes of infants and toddler, and better control of leakage from the legs and waistbands when the diaper is positioned on an infant or toddler.

This development of the disposable diaper industry, however, has increased demand for faster and more efficient disposable undergarment production. This demand is further complicated by the development of disposable infant and toddler briefs, which have a different product configuration and have different product performance requirements than disposable diapers. Also, because of the relative success of the disposable diapers and the high volume of disposable diaper products produced in manufacturing, the market for toddler briefs has generally been a much smaller subset of the infant and toddler disposable diaper market. The demand for toddler briefs in general is substantially less than the disposable diapers. Accordingly, these specially configured briefs are not normally produced on the same production line as the disposable diaper production line. Because the market demand for these briefs is less, product manufacturers are less inclined to invest in additional machinery for producing these products. The product manufacturer, however, is also pushed by retailers and consumers to provide a full-line of disposable products for infants and toddlers.

Additionally, as the nursing home care and elderly care industry has grown over the years, the elderly often have needed more and more assistance from nursing home or elderly care personnel, including urination and bowel movement assistance. Urination and bowel movement problems have also arisen among various aged adults such as loss of bladder control through childbirth or other medical reasons. Accordingly, there is a need for disposable adult undergarments, as well as the disposable infant and toddler undergarments, and an apparatus and methods for forming these undergarments.

OBJECTS AND SUMMARY OF THE INVENTION

With the foregoing in mind, it is an object of the present invention to provide a disposable undergarment forming apparatus and method for producing disposable undergarments more efficiently.

It is also an object of the present invention to provide a disposable undergarment forming apparatus and method having a higher production speed.

It is another object of the present invention to provide a disposable undergarment forming apparatus and method having the flexibility to produce both infant or toddler undergarments and adult undergarments more efficiently.

It is also another object of the present invention to provide a disposable undergarment forming apparatus and method having the flexibility to produce different undergarment configurations efficiently with only minor production line changes.

It is still another object of the present invention to provide a disposable undergarment forming apparatus and method for increasing the value and productivity of a disposable undergarment production line.

These objects and other advantageous of the present invention are provided by a disposable undergarment apparatus for forming a plurality of disposable undergarments which preferably includes core forming means for forming a stream of undergarment cores traveling along a path of travel. The core forming means includes mat securing means for securing each of a plurality of undergarment mats to a sheet of a polymeric material and first separating means positioned downstream from the mat securing means for separating the stream of undergarment cores into a plurality of individual undergarment cores. The apparatus also includes waistband forming means positioned adjacent the core forming for forming waistbands and combining means positioned downstream from the core forming means and positioned to receive the waistbands from the waistband forming means for combining the waistbands with the plurality of individual undergarment cores to thereby form a chain of a plurality of undergarments. Folding means is positioned downstream from the combining means for folding each of the plurality of undergarments of the chain. The folding means includes a core folder for folding each of the cores of the plurality of undergarments of the chain. Side connecting means is positioned downstream from the folding means for connecting at least the side waistbands of each of the plurality of undergarments of the chain, and second separating means is positioned downstream from the side sealing means for separating the chain of the plurality of undergarments into a plurality of individual disposable undergarments.

Also, an apparatus for forming disposable undergarments according to the present invention, according to one embodiment, for example, further includes core forming means having core elastic applying means for applying elastic to side peripheries of the polymeric sheet and stand-up leg gather forming means positioned adjacent the core elastic applying means for forming stand-up legs gathers on the polymeric sheet. The stand-up leg gather forming means includes leg sealing means for sealing polymeric material so as to form a liquid impervious seal for each of the stand-up leg gathers of the plurality of cores. The side connecting means preferably includes clamp conveying means positioned downstream from the folding means for clamping and conveying the chain of the plurality of undergarments to and through the side connecting means and to the second separating means. Side-entry stacking means in a particular form, for example, is positioned downstream from the second separating means for receiving a plurality of individual disposable undergarments from a side-entry position and for stacking the plurality of disposable undergarments into a predetermined stack. Position orienting means preferably is positioned between the second separating means and the side-entry stacking means for positionally orienting the plurality of individual undergarments from a generally vertical orientation to a generally horizontal orientation for side entry into the side-entry stacking means.

A disposable undergarment forming apparatus according to another specific form of the present invention also advantageously includes core orienting means positioned downstream from the core forming means for orienting each of the plurality of individual cores from a position having a lengthwise extent in a direction of the path of travel to having the lengthwise extent positioned transverse the path of travel. The waistband forming means preferably includes dividing means for dividing a continuous sheet of non-woven material into a plurality of continuous strips and strip combining means for combining strips of elastic material with the plurality of continuous strips of non-woven material. The folding means preferably includes a waistband folder positioned downstream from the combining means for folding each of the continuous waistband strips and a second folder positioned downstream from the core folder for providing a second fold, e.g., a side fold, to the folded cores of the plurality of undergarments of the chain. The apparatus according to another embodiment of the present invention can include leg forming means positioned downstream from the core forming means for forming a pair of leg openings in each of the plurality of undergarments of the chain, and wherein the side connecting means further connects the side peripheries of each of the plurality of undergarments from the waistbands to each of the pair of leg openings.

Additionally, a disposable undergarment forming apparatus according to the present invention is provided for forming a disposable undergarment. The apparatus preferably has core forming means for forming at least one undergarment core. The core forming means includes mat securing means for securing a lower surface of an undergarment mat to a sheet of a polymeric material. The apparatus also has waistband forming means for forming at least one waistband and combining means positioned downstream from the core forming means and positioned to receive the at least one waistband from the waistband forming means for securing the at least one waistband to the at least one undergarment core to thereby form at least one undergarment. Folding means is positioned downstream from the waistband securing means for folding the at least one undergarment. The folding means includes a core folder for folding the core of the undergarment. Side connecting means is positioned downstream from the folding means for connecting at least the side peripheries of the at least one waistband of the undergarment.

Methods of forming disposable undergarments are also provided according to the present invention. A method includes securing a pair of continuous strips of elastic waistband material to each of a plurality of individual undergarment cores so as to form a chain of a plurality of individual undergarments, connecting side peripheries of at least the waistband of each of the plurality of undergarments of the chain, and separating the chain of the plurality of undergarment into individual undergarments.

Another method according to the present invention includes securing elastic waistband material extending along a path of travel to each of a plurality of elongate undergarment cores having a lengthwise extent positioned transverse to the path of travel so as to form a chain of a plurality of individual undergarments, sealing side peripheries of at least the waistband of each of the plurality of undergarments of the chain, and separating the chain of the plurality of undergarment into individual undergarments. The side sealing, for example, preferably is ultrasonically sealing side peripheries of at least the waistband of disposable adult undergarment products and preferably includes ultrasonically sealing side peripheries from the waistband to the leg openings of disposable brief products.

A further method of forming a plurality of disposable undergarments according to the present invention which preferably includes forming a continuous stream of a plurality of elongate undergarment cores along a path of travel and separating the stream of the plurality of undergarment cores into a plurality of individual elongate undergarment cores intermittently-spaced along the path of travel. Each of the individual undergarment cores are then oriented so that each lengthwise extent is positioned transverse to the path of travel, and a pair of continuous strips of elastic waistband material extending along the path of travel are secured to each of the plurality of individual undergarment cores so as to form a chain of a plurality of individual undergarments. The method preferably also includes ultrasonically sealing side peripheries of at least the waistband of each of the plurality of undergarments of the chain and separating the chain of the plurality of undergarments into individual undergarments.

An apparatus and methods of the present invention advantageously provide a flexible and cost efficient disposable undergarment forming machines which can produce numerous disposable undergarments in a high speed production process. The apparatus and methods enhance current manufacturers ability to produce various configurations of undergarments in a cost efficient process, especially where the particular configurations are demanded or needed by the market but the volume, for example, is significantly less than other product configurations.

BRIEF DESCRIPTION OF THE DRAWINGS

Some of the objects, features, advantages, and uses of the present invention having been stated, others will become more apparent by referring to the following detailed description and drawings in which:

FIG. 6A is a schematic perspective view of a folder, a side connector, an undergarment separator, and a side-entry stacker of a disposable undergarment forming apparatus according to a first embodiment of the present invention;

FIG. 6B is a schematic perspective view of a folder, a side connector, an undergarment separator, and a side-entry stacker of a disposable undergarment forming apparatus according to a second embodiment of the present invention;

FIG. 7 is a schematic perspective view of a folder of a disposable undergarment forming apparatus according to the present invention;

FIG. 8 is a schematic perspective view of a clamping conveyor of a side connector of a disposable undergarment forming apparatus according to the present invention;

FIG. 10 is a schematic perspective view of an undergarment position orientor, a compression conveyor, a side entry stacker, a stacking compressor, a packaging conveyor, and a bagging device of a disposable undergarment forming apparatus according to a second embodiment of the present invention;

FIG. 11 is a schematic perspective view of a side-entry stacker of a disposable undergarment forming apparatus according to the present invention;

FIG. 12 is a fragmentary perspective view of a core of a disposable undergarment formed by a disposable undergarment forming apparatus according to the present invention; and FIG. 13 is a top plan view of an embodiment of a side connector and a side connector drive of a disposable undergarment forming apparatus according to the present invention.

DETAILED DESCRIPTION

The present invention will now be described more fully hereinafter with reference to the accompanying drawings in which preferred embodiments of the invention are shown. This invention, however, can be embodied in many different forms and should not be construed as limited to the illustrated embodiments set forth herein. Rather, applicants provide these embodiments so that this disclosure will be thorough and complete, and will fully convey the scope of the invention to those skilled in the art. Like numbers refer to like elements throughout.

Figure 1:
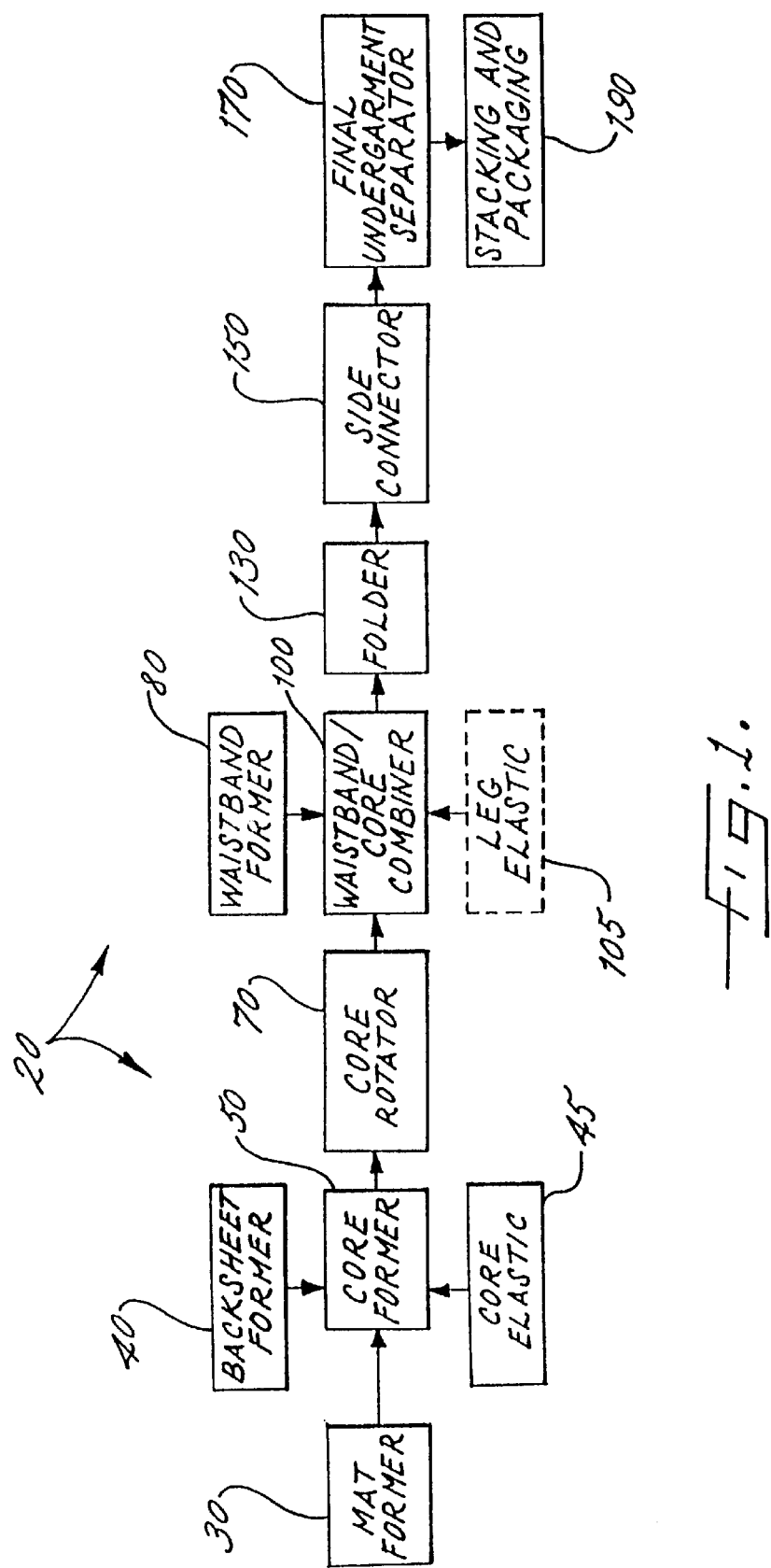
FIG. 1 is a schematic block diagram of a disposable undergarment forming apparatus according to the present invention.
Figure 2:
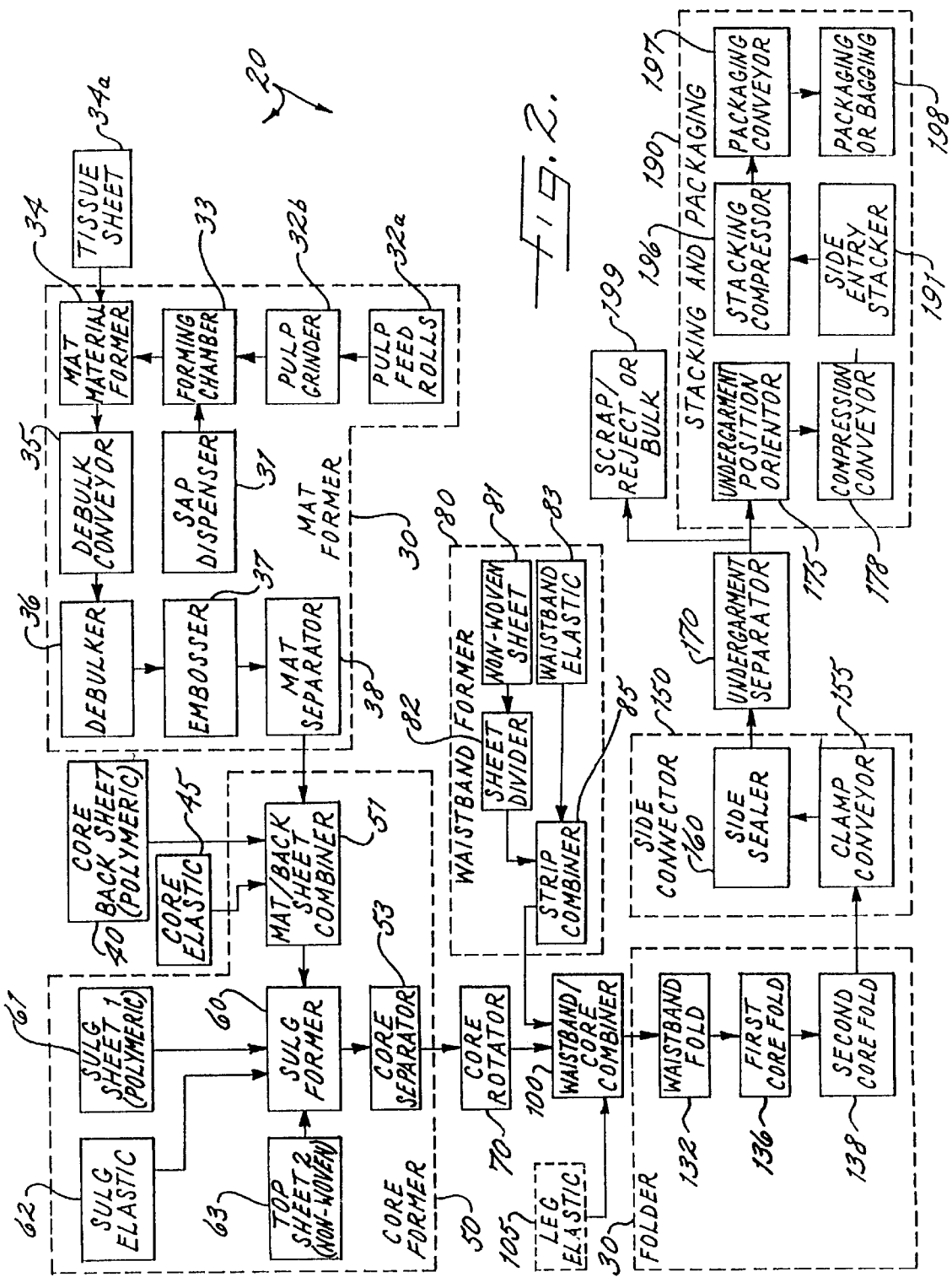
FIG. 2 is a schematic block diagram of a disposable undergarment forming apparatus according to the present invention.

FIGS. 1–2 schematically illustrate block diagrams of a disposable undergarment forming apparatus 20 for forming a plurality of disposable undergarments (see e.g., FIG. 12) according to the present invention. The apparatus 20 preferably includes a frame 25, including a plurality of frame members as illustrated, and core forming means, e.g., a core former 50, mounted to the frame 25 for forming a stream or a sheet S of a plurality of elongate undergarment cores C traveling along a path of travel P generally indicated by the flow arrows. The cores C, as well as other portions of undergarments U, preferably are conveyed or driven along the path of travel P by various conveyors which include respective conveyor drives of the apparatus 20 as understood by those skilled in the art. The apparatus 20 preferably also includes control means, such as one or more controllers, connected to the conveyors and the various other portions of the apparatus 20 described further herein for controlling various stages of the undergarment forming apparatus 20 during the formation and production of undergarments U. The controllers, e.g., controllers 162, 192, preferably are microprocessor or other computer based controls and can include a plurality of optical encoders as understood by those skilled in the art.

Figure 3:
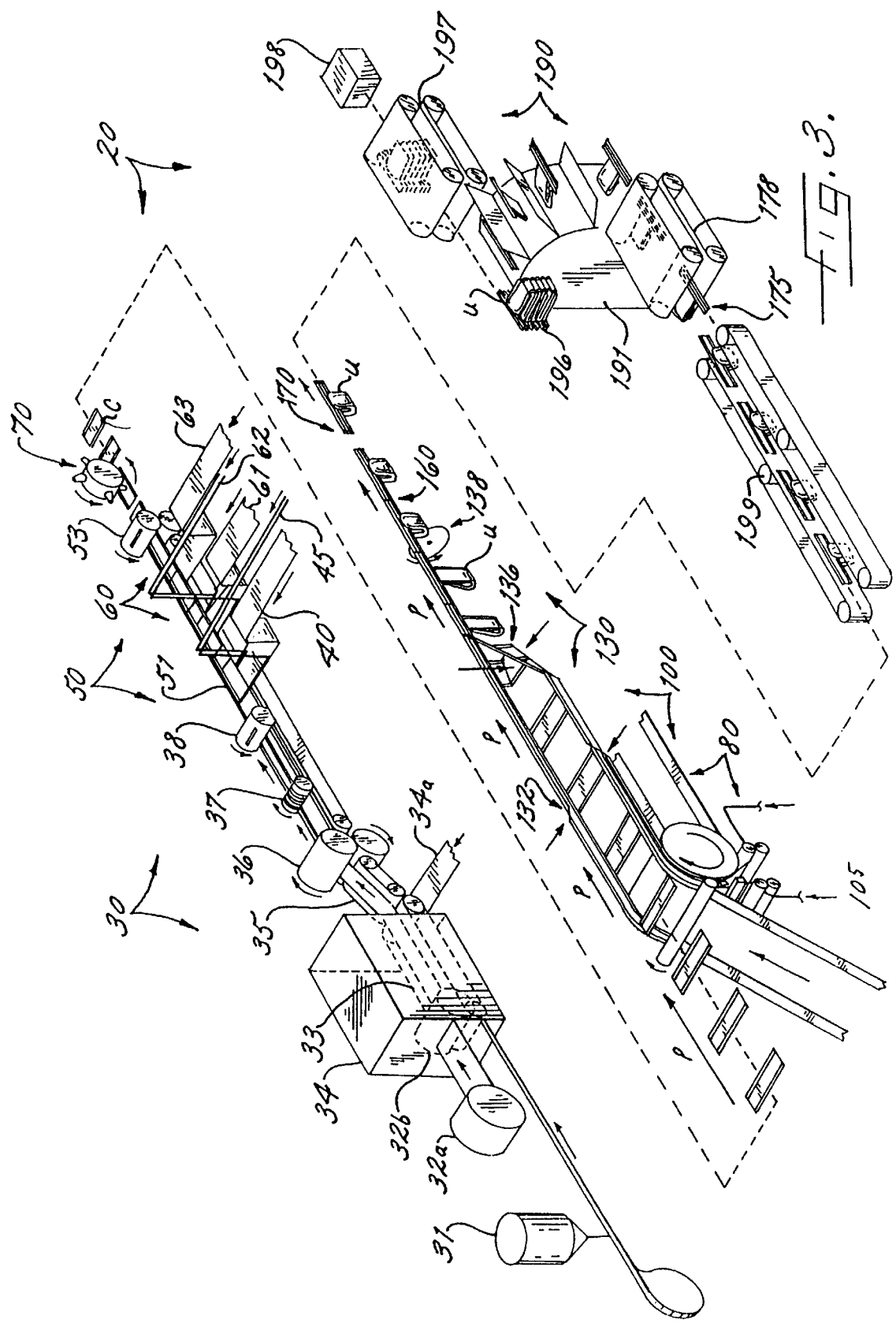
FIG. 3 is a schematic perspective view of a disposable undergarment forming apparatus according to a first embodiment of the present invention.
Figure 4:
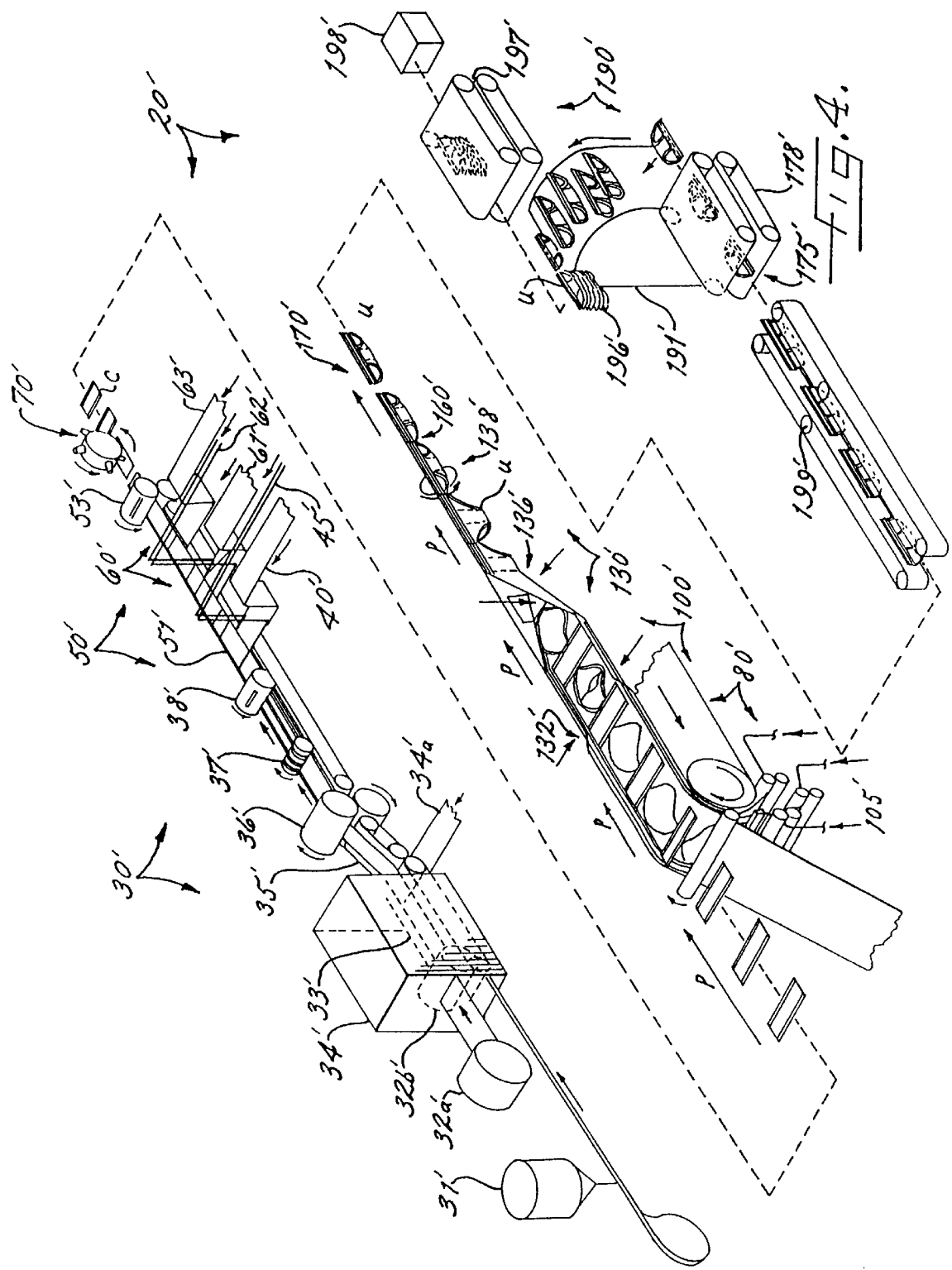
FIG. 4 is a schematic perspective view of a disposable undergarment forming apparatus according to a second embodiment of the present invention.

As best illustrated in FIGS. 1–4, mat forming means, e.g., a mat former 30, is positioned upstream from the core forming means 50 for forming a mat M for each of the cores C produced by the apparatus 20. The mat former 30, as best illustrated in FIGS. 3–4, as well as FIGS. 1–2, preferably includes a feeder 31 for feeding a super absorbent polymer ("SAP") and a pulp source 32. The pulp source 32 preferably includes rolled pulp mounted on pulp feed rolls 32a and a pulp grinder 32b for grinding the pulp. The SAP and pulp are fed to a forming chamber 33 where the pulp is mixed with the SAP to form a stream or continuous flow of bulked mat material at a mat material former 34. The mat material of the mat M forms a significant part of the core C of an undergarment and assists in forming an absorbent portion of the core C for collecting moisture such as urination from an adult or infant. A sheet of tissue from a tissue source 34a is preferably positioned to underlie the bulked mat material, and the combination is conveyed by a debulking conveyor 35 to a debulker 36 (see e.g., FIG. 12). The tissue can also be positioned to underlie the mat material and wrapped around, e.g., so as to overlie, the mat material as well. From the debulker 36, the debulked stream of mat material is embossed by an embosser 37 and cut into a plurality of individual mats M by a mat knife or mat separator 38 positioned downstream from the embosser 37.

The individual mats M are then intermittently-spaced and conveyed by a conveyor along the path P of travel to the core forming means 50. The core forming means 50 of the apparatus 20 preferably includes mat securing means, e.g., a mat/backsheet combiner 51, for securing a lower surface of each of the plurality of intermittently-spaced elongate undergarment mats M to an upper surface of a sheet S, e.g., backsheet B, of a polymeric material traveling along the path of travel P so that side lengthwise peripheries of the intermittently-spaced elongate undergarment mats M are positioned generally parallel to side lengthwise peripheries of the polymeric sheet B. The polymeric core backing sheet B is preferably supplied by a sheet source 40 such as a wound roll of the polymeric sheet material mounted on feed rolls. The undergarment mats M are preferably secured to the polymeric backing sheet B by an adhesive material such as glue from an adhesive applicator. Such adhesive applicators as described and referenced in various positions herein will be understood by those skilled in the art.

Core elastic applying means, e.g., a core elastic applicator 45, is positioned downstream from the mat securing means 51 for applying strips of elongate elastic material to the upper surfaces of the side lengthwise peripheries of the polymeric sheet B adjacent and generally parallel to the intermittently-spaced elongate undergarment mats M. The core elastic applicator 45 preferably includes a source of core elastic, a feeder for feeding the core elastic to the polymeric backing sheet B, and an adhesive applicator for applying adhesive to either the backing sheet or the core elastic to thereby secure the core elastic to the backing sheet B.

The core forming means 50 further includes stand-up leg gather forming means, illustrated as a stand-up leg gather ("SULG") former 60, positioned adjacent the core elastic applying means 54 for forming stand-up legs gathers on the polymeric sheet B, as best illustrated in FIG. 12, which inhibit liquid such as from urination from leaking from the legs of the undergarment U. Although various single-piece, three-piece, and other configurations of an SULG, as understood by those skilled in the art, can be formed by the apparatus 20 of the present invention, the stand-up leg gather forming means 60 according to the present invention preferably includes leg sealing means, e.g., a sealer 65, for sealing polymeric material so as to form a liquid impervious seal around each of the SULGs of the plurality of cores C. The sealer 65 preferably is an adhesive or heat seat applied between the layers of polymeric material (e.g., see FIG. 12).

The seal, e.g., heat or adhesive, is preferably formed between the SULG polymeric material and the polymeric backing sheet B to inhibit leakage of moisture or liquid from and around the mat material and legs.

The SULGs are formed by a first sheet of polymeric material supplied from an SULG polymeric sheet source 61, a plurality of elongate elastic strips supplied from an SULG elastic source 61, and a top sheet of non-woven material supplied from a top sheet non-woven sheet source 63. The sheet of SULG polymeric material is divided into two strips, one for each leg. A first set of strips, e.g., one or more strips, of elastic material is positioned to extend adjacent a lengthwise side periphery of the backing sheet B, and each strip of polymeric material is positioned to overlie the first set of elastic strips and extend between the lengthwise side periphery and the mat material. The seal between the polymeric sheet material as described above is formed.

The non-woven sheet material overlies and adheres to the polymeric material along each leg, but also overlies the mat material of the core C. A second set of elastic strips, e.g., one or more elastic strips, are also positioned along peripheries of each of the SULG polymeric strips adjacent the mat material. These elastic strips preferably are positioned between the non-woven sheet material and the polymeric strip. These first and second sets of elastic strips preferably are applied to the surface of the backing sheet B in an extended position so that when the strips are relaxed or retracted, the backing sheet B, the SULG polymeric strips, and the non-woven sheet gather or form gathers extending lengthwise along what will become the legs of the core C. This, for example, allows the SULGs which eventually become the SULGs of the undergarments to be stretched when positioning the undergarment on a user to thereby provide a snug and comfortable fit around the legs of a user when relaxed or retracted. The portion of the SULG polymeric strips, the second set of elastic strips, and the portion of the non-woven sheet adjacent lengthwise peripheries of the mat material are formed to extend upwardly away from the upper surface of the mat material and the backing sheet as illustrated.

The core forming means 50 also includes first separating means 53, e.g., a core separator 53 such as a knife or blade, positioned downstream from the core elastic applying means 45 for separating the stream of intermittently-spaced elongate undergarment cores C into a plurality of individual undergarment cores C. The core separator 53 preferably is a knife mounted to a drum cylinder or roll having a predetermined circumference and which overlies and periodically contacts the stream of cores C. The knife extends the length or height of the drum cylinder so as to form a relatively small cutting line. The drum cylinder is mounted to rotate so that during one rotation cycle the knife cuts the stream of cores C only one time to thereby produce a plurality of individual cores C during a corresponding plurality of rotations. It will be understood by those skilled in the art, however, that other core separator 53 configurations could be used as well such as multiple blades on a larger drum cylinder.

Additionally, the apparatus 20 includes core orienting means, e.g., a core rotator 70, positioned downstream from the core forming means 50 for orienting, e.g., preferably by rotating each core C about 90 degrees, each of the plurality of individual elongate undergarment cores C to a position having a lengthwise extent of the cores C transverse the path of travel P. The core rotator 70 preferably lifts the individual cores from the surface of the conveyor, rotates the core to a position transverse the path of travel P, and then releases the core for other downstream operations. The lifting of the core is preferably performed by a vacuum or suction system which can accommodate the lifting and rotating of a plurality of cores C so that the production line operation continues in a smooth process.

The vacuum system preferably includes a main vacuum chamber having a vacuum source connected thereto and a plurality of core lifting members arranged so that flexible tube portions of the core lifting members abuttingly contact and are in fluid communication with the vacuum chamber. The vacuum chamber provides a vacuum lift for each of the plurality of lifting members when the lifting members are in contact with the vacuum chamber.

The plurality of lifting members preferably are mounted to drive means, e.g., a cam drive and motor, so as to rotate around the main chamber. Each lifting member includes a pair of mounting arms connected to the drive means and a core plate member pivotally mounted to the pair of mounting arms. A flexible tube connects to and extends outwardly from the core plate member. Each flexible tube has a distal end thereof arranged for abuttingly contacting the vacuum chamber. The core plate preferably is arranged to be positioned so as to overlie an individual core for lifting the core for orientation when the flexible tube contacts and is in fluid communication with the vacuum chamber.

Each lifting member is arranged for rotating the core from the position having a lengthwise extent travelling in the direction of the path of travel P to the position transverse the path of travel P. Upon reaching a predetermined position, the lifting member releases the core C and continues to rotate around the main chamber so as to return for lifting another core in the production process. The pivotal mount for rotating each core plate member, for example, can be accomplished by a pivot arm fixedly connected to the core plate member for pivoting the core plate member responsive to the pivot arm. A biasing member, e.g, a compression spring, preferably is mounted to the pivot arm. The compression spring is preferably biased in a position so that the direction of the core plate member has a lengthwise extent corresponding to a direction of the path of travel P. When the core plate member arrives or is driven to a predetermined position by the drive means, the pivot arm is guided, by a guide member connected to the frame 25, so that the core plate member pivots to a position having the lengthwise extent of the core plate member now extending transverse to the path of travel P.

The orienting or rotating the cores so as to have lengthwise extents transverse the path of travel P allows for the apparatus 20 to have a reduced number of and a more narrow glue or adhesive application path for one or more glue or adhesive applicators to secure the waistbands to the cores downstream. The glue or adhesive is preferably applied before rotation of the cores. It can also allow for a reduced amount of adhesive to be used for each undergarment and thereby reduce the production costs associated with each undergarment.

Elastic waistband forming means, e.g., a waistband former 80, preferably is positioned adjacent the core rotating means 50 and positioned to form at least two continuous strips of elongate elastic material extending along the path of travel P for forming elongate elastic waistbands W. The waistband forming means preferably is formed "off-line" from the path of travel P for ease of modifying the type of waistband that can be used for a given product. It will be understood by those skilled in the art, however, that the waistband forming means 80 can also be positioned "in-line" as well. The waistband forming means 80 includes dividing means, e.g., a sheet divider 82, for dividing a continuous sheet of non-woven material supplied from a non-woven sheet source 81 into the plurality of continuous strips and strip combining means, e.g., a strip combiner 85, for combining strips of elastic material from a waistband elastic supply source 83 with the plurality of continuous strips of non-woven material.

The plurality of continuous strips as described above preferably includes four strips of non-woven material. These four strips form two pairs of continuous waistband strips. Each waistband strip has an upper and a lower non-woven strip and one or more, e.g., preferably four, elastic strips positioned therebetween. Two of the four non-woven strips preferably have greater widths than the other two non-woven strips. These two greater width non-woven strips preferably form the lower non-woven strips of the two pairs of continuous waistband strips. The one or more elastic strips preferably are only adhered to a medial portion of the lower non-woven strips so that lengthwise periphery portions of the lower non-woven strips remain unelasticized. After the upper and lower non-woven strips and the elastic strip(s) are combined, one of the non-elasticized lengthwise periphery portions of each upper non-woven strip is folded by a folding guide member so as to now overlie and adhere to at least lengthwise peripheries of the upper non-woven strip. This fold, for example, will provide a smooth closure or sealed surface to the waistband strips and will eventually downstream become the lower portion of the waistband of the undergarment as described further herein.

The one or more elastic strips preferably are adhered to and positioned between the upper and lower non-woven strips, as well as the waistband strips being adhered to the individual cores as described further herein, in an extended position so that when released to the retracted or relaxed position, the waistband strips have a plurality of gathers formed therein. This, for example, allows the waistband strips which eventually become the waistbands of the undergarments to be stretched when positioning the undergarment on a user to thereby provide a snug and comfortable fit to the waist of a user when retracted or relaxed.

Combining means, e.g., waistband/core combiner 100, is positioned downstream from the core forming means 50 and is positioned to receive the two continuous waistband strips of elongate elastic material from the elastic waistband forming means 80 along the path of travel P for respectively combining each of the two elongate elastic strips of material so as to be secured to, e.g., by using a glue or other adhesive, the respective side peripheries, e.g., lateral or widthwise sides, of each of the plurality of individual undergarment cores C traveling transverse to the path of travel to thereby form a chain of a plurality of undergarments U joined by the elongate elastic waistbands W. The combiner 100 preferably includes a plurality of feed and/or draw rolls positioned to cooperate with a conveyor which conveys the transversely positioned cores along the path of travel P. The rolls preferably feed or draw the waistband and, optionally, leg elastic to combine with the cores.

Figure 5A:
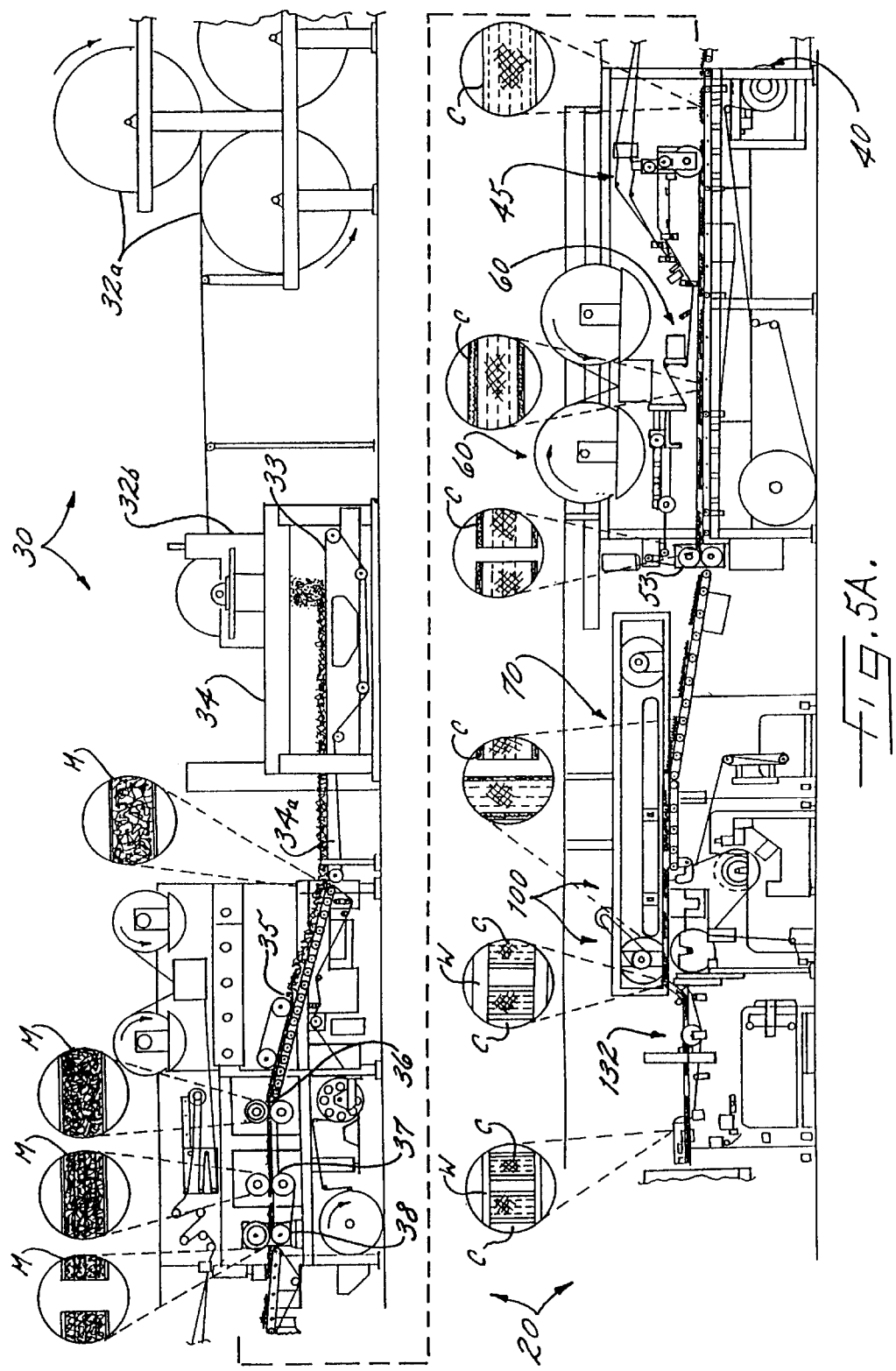
FIG. 5A is a schematic perspective view of a mat former, a core former, a core rotator, and a waistband core combiner of a disposable undergarment forming apparatus according to a first embodiment of the present invention.
Figure 5B:
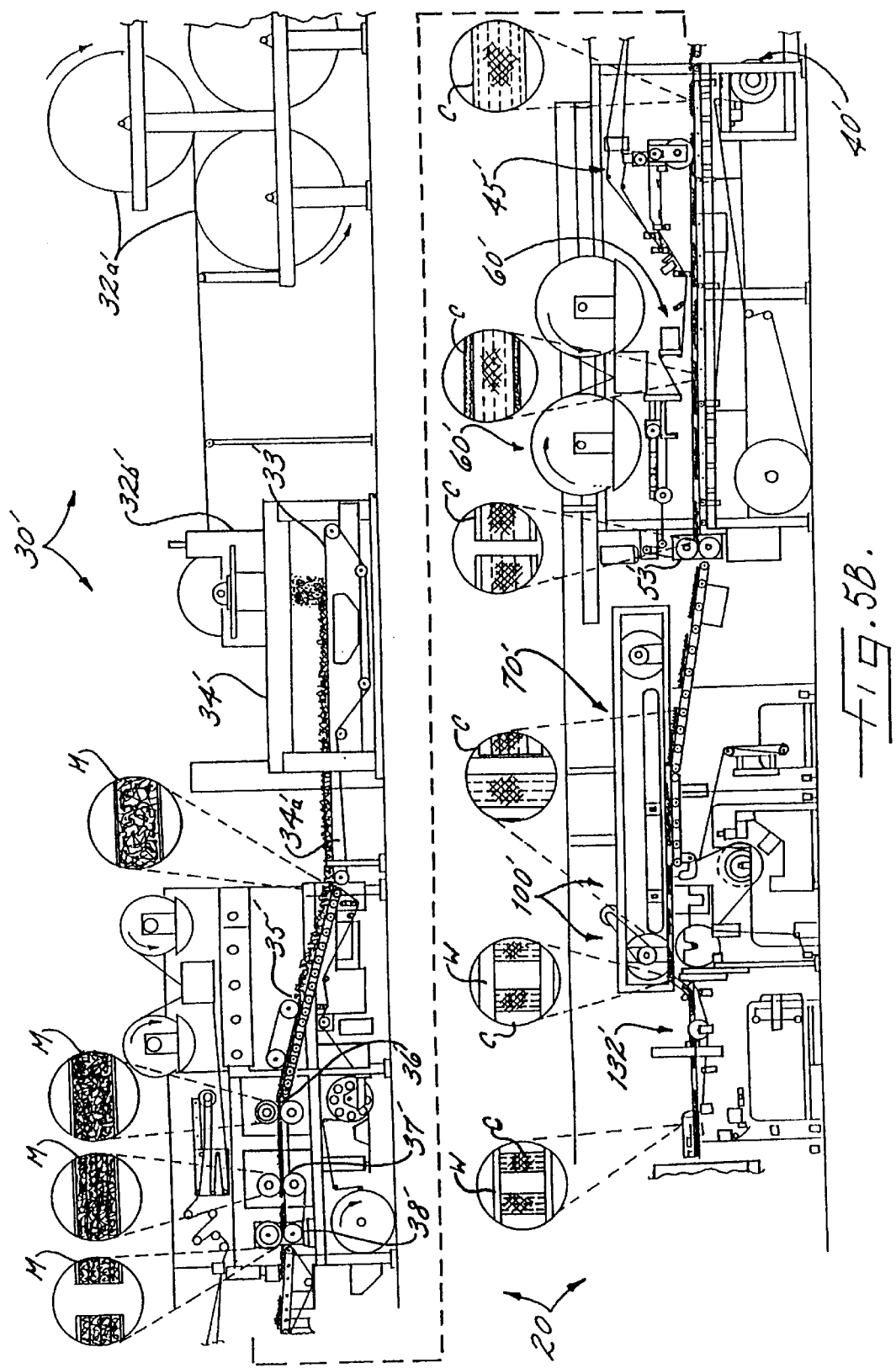
FIG. 5B is a schematic perspective view of a mat former, a core former, a core rotator, and a waistband/core combiner of a disposable undergarment forming apparatus according to a second embodiment of the present invention.

The lateral or widthwise peripheries of each individual core C preferably is glued or adhesively applied to the spaced-apart pair of waistband strips of the combiner. The lateral peripheries of each core C preferably are initially secured to the waistband strips so as to overlie the waistband strips. As will be described further herein, the greater widthwise lower strips of the waistband strips are later folded (see e.g., FIGS. 5A–5B) so that portions of what was designated as the lower non-woven strip now overlie the lateral side peripheries of the core and what was designated as the upper non-woven strip.

A leg elastic source 105, according to another embodiment of the present invention, can supply additional leg elastic at this stage of the production process, or further upstream, for combining with and into the waistband/core combiner 100. The leg elastic is preferably adhered to the lengthwise peripheries of each of the plurality of cores adjacent the SULGs in an extended position so that when the leg elastic is released to a retracted or relaxed position gathers are formed around these lengthwise peripheries. This, for example, allows the leg gathers which eventually become the legs of the undergarments to be stretched when positioning the undergarment on a user to thereby provide a snug and comfortable fit around the legs of a user when relaxed or retracted.

As particularly illustrated in FIG. 7, folding means 130 is positioned downstream from the combining means 100 for folding each of the plurality of undergarments U of the chain. The folding means, e.g., a folder 130, includes a waistband folder 132 for folding the pair of continuous waistband strips of material forming the waistbands W of the chain. The waistband folder 132 preferably includes waistband guide members which fold portions of the lower non-woven strip which do not have elastic adhered thereto so as now to overlie the upper non-woven strip and lateral peripheries of each individual core. This waistband folder 130 thereby forms both a waistband seal and a smooth inner surface for interfacing with or abuttingly contacting the waist of a user.

The folder 130 also has a core folder 136 positioned downstream from the waistband folder 132 for bi-folding each of the cores C of the plurality of undergarments U of the chain so that the two continuous strips of waistband material are positioned adjacent and in close relation to each other. The core folder 136, e.g., a first or primary core folder, preferably includes a core folding guide member which abuttingly contacts each of the plurality of individual cores which now have the lengthwise extents thereof travelling in a transverse direction to the path of travel P. The core folder 136 preferably also includes a first compressor 136a positioned downstream from the core folding guide member for compressing the core after it has been folded.

The folder 130 further has an undergarment second core folder 138, e.g., a side folder, positioned downstream from the core folder for folding each of the bi-folded cores of the plurality of undergarments U of the chain a second time. The side folder 138, or secondary folder, preferably includes a roller guide member and a belt member cooperating with the roller guide member which guide the lower extending peripheries of the bi-folded core upwardly so as to now be positioned adjacent the waistband strips as illustrated. The side folder 138 preferably also includes a second compressor 138a preferably positioned downstream from the roller guide and the belt member for compressing the core after the second or side fold. Although the side folder 138 is applicable to all types of garments, it is particularly applicable to adult undergarments which generally include cores having a greater lengthwise extent than those for infants or toddlers. The side folder 138, for example, allows the core to be folded to a more compact position for handling, stacking, and/or packaging further downstream.

As best illustrated in FIGS. 3–4, 5A–5B, and 8, side connecting means, e.g., a side connector 150, is positioned downstream from the folding means 130 for intermittently connecting at least portions of the two continuous strips of waistband material extending between each of the plurality of cores C of the plurality of undergarments U of the chain to form side peripheries of individual undergarments U. The side connecting means 150 preferably includes clamp conveying means, e.g., a clamp conveyor 155, positioned downstream from the folding means 140 for receiving, clamping, and conveying the chain of the plurality of undergarments U to and through a side sealer 160 and to second separating means, e.g., a final knife or an undergarment separator 170.

The clamp conveyor 155 preferably includes clamp driving means positioned adjacent and cooperating with the side folder for driving clamps undergarments downstream and a plurality of clamping members mounted to the clamp driving means for clamping the undergarments during conveyance downstream. The clamp driving means preferably includes a pair of cam drives mounted to the frame 25, positioned adjacent each other, and positioned so as to overlie the chain of undergarments traveling along the path of travel P. Each cam drive has a pair of spaced-apart drive wheels, e.g., sprocket or gear plates, with a drive linkage, e.g., a drive chain, mounted to and extending between each drive wheel. A motor connects to at least one of the drive wheels for rotating the drive wheel to advance the drive linkage. The plurality of clamping members preferably extend downwardly from the drive linkage and are mounted to be linearly driven by the rotation of the drive linkage about the drive wheel. The pair of cam drives are positioned so that a clamp is provided by one of the plurality of clamping members of one cam drive rotating to a position so as to align with a mating or opposite clamp on the other cam drive as illustrated. Each of the distal ends of the clamping members have roughened surfaces, e.g., rubber interface plates, which assist in the grabbing and clamping of the chain, as well as individual, undergarments when the mating clamping members from each cam drive positionally align and inhibit static or other electrical build-up between the chain and the clamp.

Preferably, the mating clamping members are arranged to align in sets of two space-apart and mating clamps so that one mating clamp of the set clamps and conveys the waistband and peripheral portions of the core of each individual undergarment and the other mating clamp of the set clamps and conveys a portion of the waistband of the chain for what will become an individual undergarment. The mating clamps preferably are position to and cooperate with the side folder to hold the side-folded undergarment in the side-folded position during conveyance.

The side sealer 160 of the side connecting means 150 preferably is connected to the frame 25 and is positioned to ultrasonically and connectively seal the intermittent portions of the waistband material of the chain as the undergarments are being conveyed. The side sealer 160 preferably includes a horn assembly 161 having a horn rotatably mounted on the frame 25 along one side of the path of travel P and an anvil assembly 166 rotatably mounted on the other side of the path of travel P and positionally aligned with the horn assembly 161 so as to seal or clamp opposing portions of the waistband strips together for sealing thereof.

Examples of such a horn and an anvil assembly 161, 166 are illustrated and described in co-pending U.S. patent application Ser. No. 07/884,804 filed on May 19, 1992 and which is hereby incorporated herein by reference. More particularly, the horn assembly and the anvil assembly, according to a first embodiment, are each mounted on a pair of space-apart drive wheels which are pivotally connected to a drive rod. Each of the drive wheels preferably is rotated by a corresponding shaft and gear arrangement, including corresponding gears, with each of the drive gears being driving by a respective pinion. An ultrasonic horn is mounted to a distal end of one drive rod, and an ultrasonic anvil is mounted to the distal end of the other drive rod. The anvil is mounted to a back plate via an air bladder which is capable of being alternately inflated and deflated from an air supply. This construction permits the anvil to be inflated outwardly toward the horn and also imparts a significant degree of flexibility and alignment to the anvil via the air bladder. The anvil preferably is also cooled to reduce glue or adhesive build up in the sealing process.

In operation, rotation of each pair of drive wheels results in the reciprocal movement of the corresponding drive rod toward the chain or web of undergarments. It will be understood by those skilled in the art that with the provision of the inflatable bladder, the anvil is imparted with a significant degree of flexibility or compressibility which thereby permits the horn and the anvil to be in contact with each other for a much greater period of time during movement of the chain through the side sealer along the path of travel P. This results in a much better forming of weld seams in the chain. Additionally, the timing of the application of the horn and anvil preferably is such so as to increase the benefits of the sealing process.

FIG. 13 illustrates an additional embodiment of a side connector 160 and a side connector drive 180 according to the present invention. In this embodiment, the side connector 160 is also an ultrasonic side sealer which includes a horn assembly 161 and an anvil assembly 166. Driving means, e.g., a side connector drive 180, is preferably connected to the side sealer 169 for driving the side sealer along the path of travel. The drive 180 preferably includes a motor 181, e.g., a servo-motor as understood by those skilled in the art, connected to the frame 25 and a wheel and a crank assembly 185 connected to the motor. The wheel and crank assembly 185 rotate corresponding to the rotation of a drive shaft 181$a$ and belt 181$b$ connected to the motor 181 as shown by the arrows. The wheel and crank assembly 185 includes a bar link 185$b$ connected to a wheel 185$a$ and connected to a portion of the side sealer 160 as illustrated. The drive 180 preferably drives the side sealer 160 along the path of travel P, e.g., upstream and downstream, as indicated by the arrows and is preferably controlled and synchronized so that the side sealer 160 is driven downstream at a speed synchronous to the speed of the clamp conveyor 155 having the chain of undergarments U positioned thereon.

More particularly, the side sealer 160 of this embodiment has a main support shaft 169 connected to the frame 25 and oriented in the same direction as the path of travel P. A pair of loading cam support shafts 168$a$, 168$b$ also connect to the frame 25 and extend transverse to, e.g., orthogonal, the main support shaft 169. A main shuttle 165 is slidably mounted to the main support shaft 169 and is connected to the wheel and crank assembly 185 of the drive 180. Each of the horn and anvil assemblies 161, 166 preferably connect to first and second cams 163$a$, 163$b$, 167$a$, 167$b$ which load and unload or open and close the respective assemblies 161, 166 during operation. The first cam 163$a$, 167$a$ has an air bag 164$a$, 164$b$, e.g., a loading air bag, connected thereto which assists in turning the first cam 163$a$, 167$a$ on and off by introducing air into the air bag 164$a$, 164$b$ or deflating the air bag 164$a$, 164$b$ as necessary and helps maintain synchronization for a smooth process. The air bags 164$a$, 164$b$ push the first cam 163$a$, 167$a$ against the second cam 163$b$, 167$b$ which preferably runs at about one-half the speed of the corresponding cam wheel, or, in other words, the second cam 163$b$, 167$b$ preferably is a double cam.

To control this portion of the operation, the air supplied to the air bags 164$a$, 164$b$ is regulated by a plurality of regulator valves and solenoid valves, preferably including quick-exhaust functions, positioned in fluid communication with the air bags 164a, 164b and an air source. This air control system preferably also controls the separate air bladder 166a or bladders of the anvil assembly 166 as described above with respect to the previous embodiment. As described above herein, by use of the inflatable bladder 166a, the anvil 166b is imparted with a significant degree of flexibility or compressibility which thereby permits the horn 161a and the anvil 166b to be in contact with each other for a much greater period of time during movement of the undergarment chain through the side sealer 160 along the path of travel P. The second cam 163b, 167b assists with the opening and closing of the horn and anvil assemblies 161, 166 after the main shuttle speed synchronizes with the clamp conveyor speed. The horn and anvil assemblies 161, 166 are each connected to the second cam 163b, 167b and each slidably mount to a pair of spaced-apart assembly support members 188a, 188b, 189a, 189b as illustrated for movement in a direction toward the product as shown by the arrows.

After the main shuttle 165 and the horn and anvil assemblies 161, 166 are positioned upstream and begin to move downstream at a speed synchronized with the clamp conveyor speed, the horn 161a and the anvil 166b close and hold side periphery portions of the waistband material, e.g., pair of waistband material. The assemblies 161, 166 are energized to provide ultrasonic energy to the material positioned between the horn 161a and the anvil 166b. The material melts and the ultrasonic energy is stopped. The horn and anvil 161a, 166b, however, remain closed so that the material positioned therebetween will cool and resolidify to thereby form a seal or bond between the pair of waistband material.

As best illustrated in FIGS. 6A–6B, second separating means, e.g., an undergarment separator 170, is positioned downstream from the side connecting means 160 for separating the connective seal of the portions of the continuous strips of waistband material of the chain into a plurality of individual disposable undergarments U. The second separating means is preferably a final knife fixedly mounted to the frame 25 and arranged to periodically cut the chain of the plurality of undergarments U. It will be understood by those skilled in the art, however, that other undergarment separator 170 configurations, as well as the other separators described herein, could be used as well, including various blade configurations, optical configurations (e.g., laser), and wire-type cutter configurations. The driving means of the side connector preferably is electrically connected to and tracks with or is synchronized with the undergarment separator 170 so that the position and timing for cutting or separating the chain into individual undergarments advantageously occurs at the right time and position on the seal of the waistband material.

As best illustrated in FIGS. 2 and 9–11, stacking and packaging means 190 is positioned downstream from the undergarment separator 170 for stacking and packaging the individual undergarments U produced. The stacking and packaging means 190 preferably includes position orientating means, e.g., a position orientor 175, positioned downstream from the second separating means 170 for positionally orienting the plurality of individual undergarments U from a generally vertical orientation to the generally horizontal orientation for side-entry stacking as illustrated. The individual undergarments U are compressed and conveyed by a compression conveyor 178 to a position for stacking. The compression conveyor 178 preferably includes a compression conveying drive, a plurality of compression rolls connected to the drive, and a plurality of belts slidably mounted to the rolls. During the driving of the rolls by the conveying drive, the belts compress and convey the individual undergarments along the path of travel P to the stacking means positioned downstream therefrom.

Figure 9:
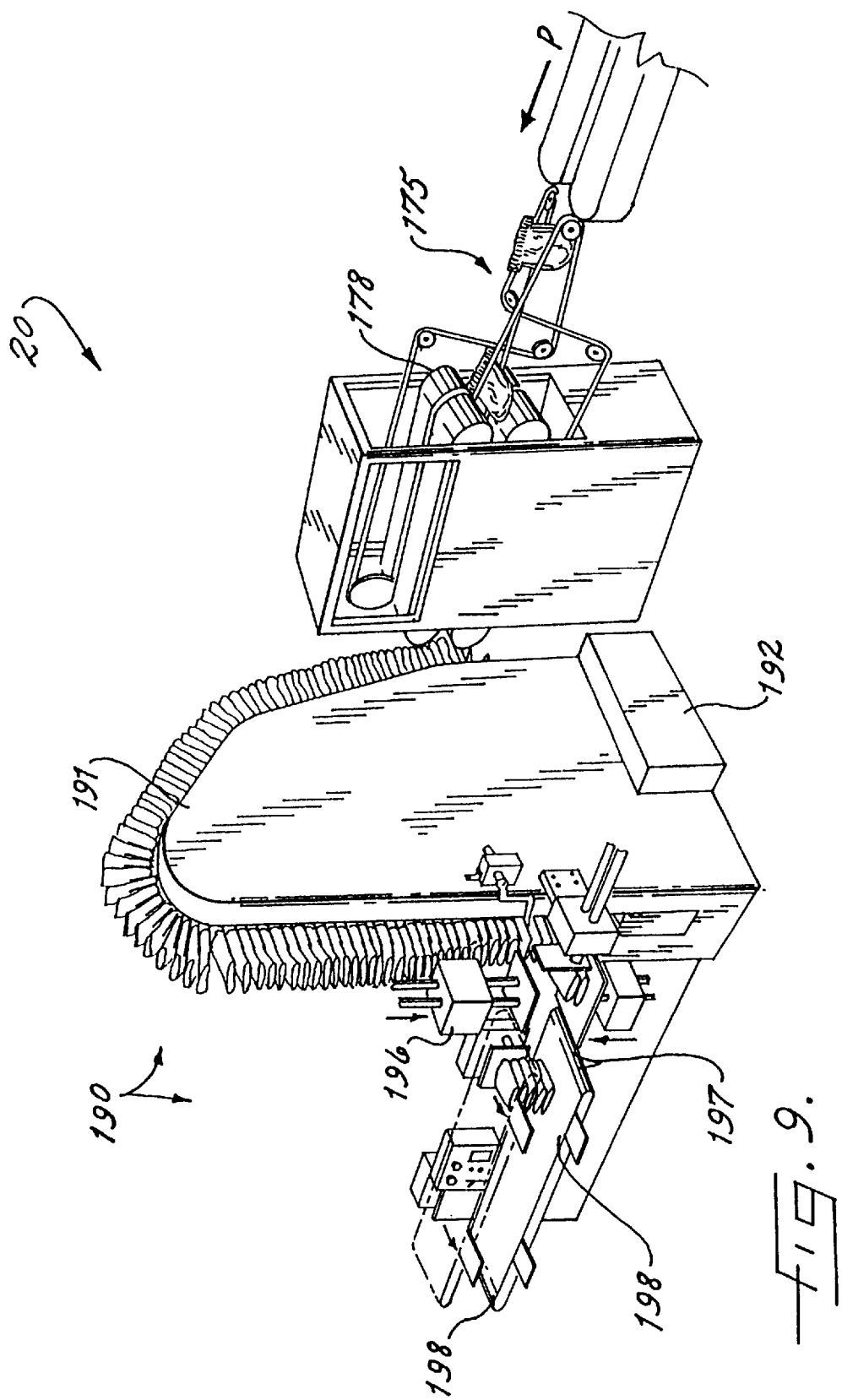
FIG. 9 is a schematic perspective view of an undergarment position orientor, a compression conveyor, a side entry stacker, a stacking compressor, a packaging conveyor, and a bagging device of a disposable undergarment forming apparatus according to a first embodiment of the present invention.

Side-entry stacking means, e.g., a side-entry stacker 191, of the stacking and packaging means, as illustrated in FIGS. 9–11, is positioned downstream from the second separating means 170, the position orienting means 175, and the compression conveyor 178 for receiving a plurality of individual disposable undergarments U from the generally horizontal side-entry position and for stacking the plurality of disposable undergarments U into a predetermined stack. The side-entry stacker 190 is preferably positioned transverse the path of travel P so as to advantageously provide a shorter linear path of travel and shorter footprint for the apparatus 20. The stacker 190 preferably includes a base and a plurality of space-apart guiding arms rotatably mounted to the base. The side-entry stacker 190 can also include a stop member 193 positioned to stop each of the plurality of compressed undergarments in a predetermined stop position after being conveyed by the compression conveyor 178. The spaced-apart guiding arms 191a then rotate adjacent the predetermined stop position and individually lift each of the undergarments so that the undergarments are positioned between the guiding arms and transported to a stacker output position which provides stacks of undergarments. The stacker also preferably includes a controller 192 for controlling the rotating guiding arms 191a and for tracking and/or counting the individual undergarments U. The controller 192 also allows an operator to set the number of undergarments to be arranged in the stacks for various sized or types of packaging or bagging.

After the plurality of individual undergarments U are stacked, the stack of undergarments U is compressed by a stacking compressor 196 of the side-entry stacker and conveyed by a packaging conveyor 197 of the stacking and packaging means 190 to a position for packaging or bagging 198. The packaging or bagging means of the stacking and packaging means 190 preferably includes a loader 198a as understood by those skilled in the art which assists in the bagging of the stack of undergarments U by production process personnel such as designated undergarment baggers.

Preferably, a scrap/reject or bulk receiving source 199 is also positioned between the undergarment separator 170 and the stacking and packaging 190. This scrap/reject or bulk receiving source 199 also provides flexibility in the operation of the apparatus 20 as an outlet for a jam, a line down, or other operational problems that may arise.

In a second embodiment of the present invention as particularly illustrated in FIGS. 4 and 6B, an apparatus 20' according to the present invention preferably includes leg forming means, e.g., a leg former 95, positioned downstream from the core forming means for forming a pair of leg openings in each of the plurality of undergarments of the chain. This particular embodiment forms a brief product preferably used by an adult, but can also be used by a toddler. The leg forming means 95 includes layer applying means for applying a continuous layer of non-woven material so as to underlie each of the plurality of individual undergarment cores U, leg elastic applying means 105 positioned downstream from the layer applying means for applying leg elastic between the layer of non-woven material and the waistbands, and leg cutting means 125 positioned downstream from the layer applying means for cutting the pair of leg openings in the layer of non-woven material. The side connecting means 150, e.g., a side sealer 160 as described above herein, according to this second embodiment, further connects the side peripheries of each of the plurality of undergarments from the waistbands, along the side peripheries of the layer of non-woven material, and to each of the pair of leg openings.

As illustrated in FIGS. 1–13 methods of forming disposable undergarments U are also provided according to the present invention. A method includes securing a pair of continuous strips of elastic waistband material to each of a plurality of individual undergarment cores C so as to form a chain of a plurality of individual undergarments U, connecting side peripheries of at least the waistband of each of the plurality of undergarments U of the chain, and separating the chain of the plurality of undergarment into individual undergarments.

The method can also include rotating each of the plurality of individual cores C, e.g., see FIGS. 3–5B, to a position having a lengthwise extent transverse a path of travel P of the continuous strips, conveying the chain of the plurality of undergarments for side sealing at least the waistband of each of the plurality of undergarments U of the chain, and driving a side sealer 160 for sealing side peripheries of a waistband of an undergarment at a speed synchronous to the conveying speed. The plurality of separated individual undergarments U can be positionally oriented from a generally vertical orientation to a generally horizontal orientation (see e.g., FIGS. 9–10). The plurality of individual disposable undergarments U are then preferably received from a side-entry position and stacking the plurality of disposable undergarments U into a predetermined stack.

The method can further include dividing a continuous sheet of non-woven material into a plurality of continuous strips and combining strips of elastic material with the plurality of continuous strips of non-woven material so as to form the pair of continuous strips of elastic waistband material. Additionally, the cores C of each of the plurality of undergarments U of the chain can be folded and a second fold such as a side fold applied to each of the folded cores of the plurality of undergarments of the chain prior to the step of sealing side peripheries of at least the waistbands. In an alternative embodiment, a pair of leg openings in each of the plurality of undergarments of the chain and sealing the side peripheries of each of the plurality of undergarments from the waistbands to each of the pair of leg openings.

Another method according to the present invention includes securing elastic waistband material extending along a path of travel P to each of a plurality of elongate undergarment cores C having a lengthwise extent positioned transverse to the path of travel so as to form a chain of a plurality of individual undergarments U, sealing side peripheries of at least the waistband of each of the plurality of undergarments U of the chain, and separating the chain of the plurality of undergarment into individual undergarments U. The side sealing, for example, preferably is ultrasonically sealing side peripheries of at least the waistband of disposable adult undergarment products and preferably includes ultrasonically sealing side peripheries from the waistband to the leg openings of disposable brief products. Additional method steps described above may also be used in this method as well.

Many modifications and other embodiments of the invention will come to the mind of one skilled in the art having the benefit of the teachings presented in the foregoing descriptions and the associated drawings. Accordingly, it is understood that the invention is not to be limited to the illustrated embodiments disclosed, and that the modifications and embodiments are intended to be included within the spirit and scope of the invention as described in the foregoing specification and as defined in the appended claims.

What is claimed is:

1. A method of forming a plurality of disposable undergarments, the method comprising:

securing an elastic waistband extending along a path of travel to each of a plurality of elongate undergarment cores having a lengthwise extent positioned transverse to the path of travel so as to form a chain of a plurality of individual undergarments;

folding the elongate undergarment cores along a fold line as the cores move along a substantially horizontal path of travel so that the lengthwise extent of each of the cores is in a substantially vertical position;

sealing side peripheries of at least the waistband of each of the plurality of undergarments of the chain;

separating the chain of the plurality of undergarments into individual undergarments; and controllably positioning the separated individual undergarments from a substantially vertical orientation to a substantially horizontal orientation as the undergarments move along the substantially horizontal path of travel.

2. A method as defined in claim 1, further comprising clamping and conveying the chain of the plurality of undergarments for side sealing at least the waistband of each of the plurality of undergarments of the chain and driving a side sealer for sealing side peripheries of the waistband material of an undergarment at a speed synchronous to the conveying speed.

3. A method as defined in claim 1, further comprising receiving the plurality of individual disposable undergarments from a side-entry position and stacking the plurality of disposable undergarments into a predetermined stack.

4. A method as defined in claim 3, further comprising dividing a continuous sheet of non-woven material into a plurality of continuous strips and combining strips of elastic material with the plurality of continuous strips of non-woven material so as to form a pair of continuous strips of elastic waistband material.

5. A method as defined in claim 4, further comprising folding each of the pair of continuous waistband strips, folding the cores of each of the plurality of undergarments of the chain, and side folding the folded cores of the plurality of undergarments of the chain prior to the step of sealing side peripheries of at least the waistbands.

6. A method as defined in claim 5, further comprising forming a pair of leg openings in each of the plurality of undergarments of the chain and sealing the side peripheries of each of the plurality of undergarments from the waistbands to each of the pair of leg openings.

* * * * *